United States Patent [19]

Bielmeier et al.

[11] Patent Number: 5,380,932
[45] Date of Patent: Jan. 10, 1995

[54] PROCESS FOR PRODUCING METHACRYLIC ACID AND METHACROLEIN BY OXIDATION OF ISOBUTANE WITH MOLYBDENUM HETEROPOLY ACID CATALYST

[75] Inventors: Ernst Bielmeier, Griesheim; Thomas Haeberle, Einhausen; Hermann-Josef Siegert, Seeheim-Jugenheim; Wilhelm Gruber, Darmstadt, all of Germany

[73] Assignee: Roehm GmbH Chemische Fabrik, Darmstadt, Germany

[21] Appl. No.: 156,822

[22] Filed: Nov. 24, 1993

[30] Foreign Application Priority Data

Nov. 28, 1992 [DE] Germany ............... 4240085

[51] Int. Cl.$^6$ ............... C07C 51/25; C07C 57/04
[52] U.S. Cl. ............... 562/543; 562/512.2; 562/523
[58] Field of Search ............... 562/543, 512.2, 523

[56] References Cited

U.S. PATENT DOCUMENTS

| | | | |
|---|---|---|---|
| 4,606,863 | 8/1986 | Nakazawa et al. | 562/543 X |
| 5,294,739 | 3/1994 | Kraushaar-Czarnetzki et al. | 562/543 |
| 5,300,682 | 4/1994 | Blum et al. | 562/512.2 |

FOREIGN PATENT DOCUMENTS

| | | |
|---|---|---|
| 0005769 | 12/1979 | European Pat. Off. |
| 0010902A1 | 5/1980 | European Pat. Off. |
| 0113084B1 | 12/1983 | European Pat. Off. |
| 0284947 | 10/1988 | European Pat. Off. |
| 0376177A2 | 7/1990 | European Pat. Off. |
| 0418657A2 | 3/1991 | European Pat. Off. |
| 0425666A1 | 5/1991 | European Pat. Off. |
| 2722375 | 12/1977 | Germany. |
| 3010434A1 | 11/1980 | Germany. |
| 4113423 | 10/1992 | Germany. |

*Primary Examiner*—Arthur C. Prescott
*Attorney, Agent, or Firm*—Oblon, Spivak, McClelland, Maier & Neustadt

[57] ABSTRACT

The present invention relates to a process for the production of methacrylic acid and methacrolein by means of gas phase oxidation of isobutane in the gaseous phase at 250° to 450° C. on molybdenum heteropoly acid catalysts that are made up of $CU_aH_bP_cMo_dV_eO_f$ heteropoly acid compounds (I), where a=0.1 to 1, b=0 to 7.8, c=0.8 to 1.2, d=9 to 12, e=0.5 to 3, and f depends on the molar numbers a to e, and/or the heteropoly acid $H_8PMo_{10}VO_{39}$ (II) or its anhydride $PMo_{10}VO_{35}$ (III).

5 Claims, No Drawings

PROCESS FOR PRODUCING METHACRYLIC ACID AND METHACROLEIN BY OXIDATION OF ISOBUTANE WITH MOLYBDENUM HETEROPOLY ACID CATALYST

BACKGROUND OF THE INVENTION

1. Field of the Invention

The present invention relates to the production of methacrylic acid and methacrolein by means of a gas phase oxidation of isobutane with a molybdenum heteropoly acid catalyst.

2. Discussion of the Background

Methacrylic acid can be made by gas phase oxidation of various starting materials, such as isobutylene, methacrolein, isobutyric acid, and isobutane. The oxidation reactions with molecular oxygen are managed selectively on solid-body catalysts, retaining the molecular carbon arrangement. These solid catalysts, almost without exception, contain molybdenum in an oxidic bond as an essential constituent, along with other elements that influence the activity and selectivity of the catalysts. Particularly important are catalysts that are made or built up on the basis of heteropoly acids of molybdenum with phosphorus as the central atom.

According to DE-OS 27 22 375, one may, for example, use $H_5PMo_{10}V_2O_{40}$-heteropoly-acid-containing catalysts, among other things, as well as copper-containing catalysts, both for the oxidation of methacrolein into methacrylic acid, and for the oxydehydration of isobutyric acid or its esters into methacrylic acid or its esters.

According to EP-B 0 005 769, catalysts having the formula $Mo_aV_bP_cX_dO_e$, which have a heteropoly acid structure, are used for the oxidation of isobutylene and/or tertbutanol into methacrolein and methacrylic acid. A process for the oxidation of methacrolein into methacrylic acid with catalysts of the same kind is described in DE-OS 30 10 434.

The heteropoly acid having the formula $H_8PMo_{10}VO_{39}$ and its anhydride $PMo_{10}VO_{35}$, according to EP-B 0 194 541, are suitable as more temperature-stable heteropoly acid catalysts in oxidation reactions, such as oxidation of the olefins propylene and isobutylene into the corresponding unsaturated aldehydes acrolein and methacrolein, and also their further oxidation into acrylic acid and methacrylic acid, and in oxydehydration reactions of isobutyric acid or its esters into methacrylic acid or its esters.

According to EP-B 0 113 084, copper derivatives of this heteropoly acid anhydride, for example, $Cu_{0.2}PMo_{10}VO_{35.2}$ and also copper derivatives of other heteropoly acids, such as $H_5PMo_{10}V_2O_{40}$-heteropoly acid, are very selective catalysts in the oxydehydration of isobutyric acid into methacrylic acid.

EP-A 284 947 mentions the manufacture of molybdenum heteropoly acid oxidation catalysts of the kind described above. Here, one uses water-soluble, practically non-volatile organic compounds, especially polymers, which are then calcined at 150°–400° C. in the presence of oxygen. Catalysts made in this fashion stand out by their improved long-term behavior in the course of oxydehydration of isobutyric acid into methacrylic acid.

Furthermore, EP-A 0 376 177 proposes a process for making methacrylic acid by oxidation of methacrolein on oxidic catalysts having the formula $MO_{12}P_aV_bC_sAs_dCu_eX_fY_gO_x$. During the shaping of the catalyst, one can add known carbon-containing compounds as slip additives. In addition, one can add forming expedience and reinforcing agents, such as inorganic microfibers (for example, glass or asbestos). The catalysts are calcined at temperatures of 180° to 480° C., possibly in an air atmosphere.

Catalysts for selective oxidations generally have a small inside surface; i.e., the catalyst grain is provided with relatively few pores, or they are made with porous carriers with wide pores in the interior of the carrier material in which the catalytic material is then embedded. Such carriers are very permeable for a diffusion stream for the transport of matter and energy to the catalytically active material. Combinations of substances containing molybdenum, vanadium, phosphorus, and oxygen with carriers having a porosity of 10 to 80% and an interior surface of less than 1 $m^2/g$ are described as catalysts for the oxydehydration of isobutyric acid into methacrylic acid in DE-OS 31 45 091.

Finally, DE-OS 41 13 423 describes oxidation catalysts with molybdenum, phosphorus, and vanadium as essential elements in an oxidic form and on a heteropoly acid base which contain channels formed by burning out organic fibers. They are used for the oxidation of propylene or isobutylene into acrolein or methacrolein, for their further oxidation into the corresponding (meth)acrylic acid, and for the oxydehydration of isobutyric acid or its lower esters into methacrylic acid or its esters.

The oxidation of isobutane into methacrylic acid and methacrolein on oxidic solid catalysts that contain molybdenum, antimony and phosphorus is known from EP-A 0 010 902, according to which one gets, with approximately 10% isobutane conversion, methacrylic acid with approximately 50% selectivity and methacrolein with about 20% selectivity. According to JP 0 320 237, isobutane is converted into methacrolein with 9.5% conversion in 51.4% selectivity on an oxide contact with phosphorus, vanadium, molybdenum, antimony and copper.

Solid catalysts made of heteropoly acids of molybdenum and their salt derivatives are also suitable for selective isobutane oxidation. According to EP-A 0 418 657, these are phosphomolybdic heteropoly acid salts that forcibly contain at least one element of rubidium, cesium and thallium. Optionally, these heteropoly acid salts may forcibly contain vanadium, arsenic, copper or another metal.

EP-A 0 425 666 describes a process for making methacrylic acid and methacrolein by oxidation of isobutane, performed on catalysts made from molybdenum heteropoly acids with phosphorus and/or arsenic as the central atom. The catalysts forcibly contain at least one constituent from the group of an alkali metal, an alkaline earth metal and thallium, plus vanadium and/or copper, and optionally, additional metallic elements.

Catalysts for isobutane oxidation made from heteropoly acids of molybdenum with phosphorus and/or arsenic as a central atom and without vanadium as a molybdenum-replacing coordinating periphery atom are described in Japanese patent application JP 02 42 033, according to which copper is also contained therein obligatorily, plus JP 02 42 034 and JP 62 132 832, as well as JP 63 145 249, with the last two applications mentioned covering variations of the process.

The attainable yield of end product, the conversion of a starting material and/or the attainable space-time yield are important quality characteristics of a catalyst, in conjunction with a certain conversion. However, the selectivity (i.e., the quotient of yield and conversion) of a catalyst indicates what part of the starting material was actually converted into the desired end product. As a result, the selectivity is considered the most important quality characteristic of the catalyst. Prior approaches to the oxidation of isobutane into methacrylic acid and methacrolein left considerable room for improvement in selectivity, and therefore, were deficient with regard to the selectivity of the catalyst and process.

SUMMARY OF THE INVENTION

Accordingly, one object of the present invention is to provide a novel process for preparing methacrylic acid and methacrolein by oxidizing isobutane with a molybdenum heteropoly acid catalyst, which increases the selectivity of the oxidation process and catalyst.

This object and others are attained by the present invention by using a heteropoly acid catalyst containing molybdenum and vanadium with phosphorus as the central atom, without the presence of any other cationic compounds, and especially without the presence of alkali metal and alkaline earth metal compounds. The present catalyst may also contain copper, or may be copper-free, and may be exemplified by a catalyst such as $H_8PMo_{10}VO_{39}$-heteropoly acid or its anhydride, $PMo_{10}VO_{35}$.

DETAILED DESCRIPTION OF THE PREFERRED EMBODIMENTS

The present invention accordingly relates to a process for making methacrylic acid and methacrolein, comprising oxidizing isobutane with molecular oxygen in the gas phase at a temperature of from 250° to 450° C. on a solid heteropoly acid catalyst having the formula:

$$Cu_aH_bP_cMo_dV_eO_f \qquad (I)$$

where a=0.1 to 1, b=0 to 7.8, c=0.8 to 1.2, above all 1, d=9 to 12, above all 10 or 11, e=0.5 to 3, above all 1 or 2, and f depends on the molar numbers a to e; and/or the formula $$H_8PMo_{10}VO_{39} \qquad (II)$$

or its anhydride $$PMo_{10}VO_{35} \qquad (III).$$

Using the solid catalysts made from compounds I and/or II or III, one can attain selectivities that are definitely over 80% and peak selectivity values of around 90%, for the sum of methacrylic acid and methacrolein, compared to a maximum value of 75% as indicated in Example 2 of EP-A 0 425 666.

In particular, using catalysts made from compounds II or III according to the present invention, one can perform the oxidation of isobutane at a temperature of more than 350° C. In contrast to other known heteropoly acid catalysts, the present catalysts are thermally more stable than the catalysts used in EP-A 0 425 666 and EP-A 0 418 657.

The selectivities of methacrylic acid and methacrolein, as valuable substances, can be influenced in terms of further increases during the process if the catalysts are made with heteropoly acid components I and/or II or III in the presence of combustible, pore-forming, fibrous additives.

The conversion of isobutane depends, among other things, on the molar ratio of isobutane to oxygen. The conversion and the space-time yields of methacrylic acid and methacrolein can be increased by raising either the initial isobutane concentration or the oxygen portion in the gas mixture to be converted, which can be done advantageously by using oxygen-enriched air.

Active Components of the Present Catalyst

The present catalysts contain substances in which molybdenum, phosphorus, vanadium, and in catalysts according to the formula of compound (I), copper oxides are present as the active material. The present catalysts are made up of compound (I) having the chemical composition $Cu_aH_bPMo_dV_eO_f$, with the above-mentioned meanings for a, b, c, d, e, and f. In the present catalyst, f preferably depends on the molar numbers a, b, c, d and e, such that:

$$f=(\tfrac{1}{2})a+(\tfrac{1}{2})b+(5/2)c+3d+(5/2)e$$

Alternatively, the present catalyst may be made from $H_8PMo_{10}VO_{39}$ (II) or from $PMo_{10}VO_{35}$ (III), alone or in combination with compound (I). The present catalysts of the formula (I) are vanadium derivatives of phosphomolybdic heteropoly acids that can be described by the chemical formula $H_{3+x}PMo_{12-x}V_xO_{40}$ where x=1, 2 or 3, and that forcibly contain copper. Alternatively, the present catalysts of the formula (II) or (III) are $H_8PMo_{10}VO_{39}$ heteropoly acid or its anhydride $PMo_{10}VO_{35}$, as well as copper derivatives of this heteropoly acid and its anhydride.

To make the catalysts used in the present process, one can obtain the heteropoly acid compounds from oxides of the individual components, such as, for example, $MoO_3$, $V_2O_5$, $H_3PO_4$, $CuO$, or from salts that can be decomposed at higher temperatures, such as $(NH_4)_2MoO_4$, $NH_4VO_3$, $Cu(NO_3)_2$, according to known processes. Such production methods are described by way of example in DE-OS 27 22 375 and in EP-B 0 046 840.

The goal of using more selective catalysts in the oxidation of isobutane is attained above all when the heteropoly acids (I) are made by hydrothermal conversion of oxidic compounds of molybdenum, vanadium, phosphorus and copper, as described particularly in EP-B 0 113 084, and when heteropoly acid (II) or its anhydride (III) is made hydrothermally according to EP-B 0 194 541.

The term "hydrothermal conversion" was used in DE-OS 27 22 375 to describe the formation of an Mo—V-phosphate acid from the oxides of Mo, V and P in an aqueous phase at 60° C. or more during a reaction time that mostly lasted several hours. In place of the oxides, one can also use ammonium molybdate or ammonium vanadate to form heteropoly acids. However, ammonium compounds have proven to be as disadvantageous as alkali compounds when it comes to catalyst properties. Therefore, ammonium compounds are preferably not used. The development of heteropoly acid takes place in a particularly favorable manner in a boiling aqueous solution under standard pressure, and can be recognized by the gradual deep red coloration of the aqueous solution.

The term "heteropoly acid" in the present application is not to be confined to integral stoichiometric relationships. In the pure heteropoly acids, one finds above all an Mo:P ratio of 11:1 or 10:1. However, even somewhat larger or smaller Mo:P ratios lead to good catalysts. If there is a P-shortfall in the aqueous phase, then presumably one also encounters Mo-isopoly acids along with the actual heteropoly acids. The entire acid mixture, made in the presence of Cu in the case of compounds of the formula (I), is referred to here as heteropoly acid.

Examples of copper-containing compositions having the formula (I) include $Cu_{0.2}H_{3.6}PMo_{11}VO_{40}$, $Cu_{0.4}H_{4.2}PMo_{10}V_2O_{40}$, $Cu_{0.2}H_{7.6}PMo_{10}VO_{39}$, and $CuH_6PMo_{10}VO_{39}$.

Fabricating the Catalyst

The Cu-containing Mo—V—P-heteropoly acid solution and/or the $H_8PMo_{10}VO_{39}$ solution can be dried as such in the absence of solids, and the residue can be calcined and used as the catalyst. Often one prefers to dilute (mix or support) the catalyst with an inert material, such as fine-particle $SiO_2$, $Al_2O_3$, $ZrO_2$, silicon carbide, and the like, and to process it into a granule contact material (i.e., something that can be made and/or processed by extrusion, pressing, pelletizing, or granulation). The catalyst is preferably mixed or supported with an amount of the inert carrier sufficient to provide a weight ratio of the catalyst to the inert carrier of, for example, from 1:0.1 to 1:10.

For this purpose, the mixture can be turned into dough with water or an aqueous solution. When pelletizing hard, essentially non-porous inert carrier bodies, one preferably starts with a rough surface, then one can apply the catalyst as a thin shell, according to the sugar-coating technique. For this purpose, one applies the powdery catalyst and possibly a bonding agent-containing liquid upon the carrier bodies (for example, little ceramic balls) in a drum that rotates in a slanted position. The pellets thus made are then dried. If necessary or desired to obtain a predetermined particle size, the entire procedure may be repeated several times.

The aqueous solution of heteropoly acid can also be dried in the presence of a solid catalyst carrier material. The above-mentioned inert materials are suitable for use as a solid catalyst carrier material. The carrier substances can have a porosity of less than 10% by volume and/or an internal surface of advantageously from 0.1 to 10 $m_2/g$. The portion of these carriers can be from 5 to 95% by weight, relative to the total weight of the catalyst.

The carrier material, for example, is mixed with the heteropoly acid solution to form a magma. Thereafter, it is evaporated to dryness by heating to the boiling point of the solution (i.e., at temperatures of, for example, from 50° to 110° C.), and if desired, at a reduced pressure (e.g., from 400 to 0.1 torr). Alternatively, large porous carrier particles, with a side length or diameter of, for example, from 2 to 10 mm, are soaked with the solution of heteropoly acid, as a result of which one obtains catalysts with up to about 50% by weight of catalytically active material in the particles. Examples of suitable large porous carrier particles include zirconia, silicon carbide and silica, preferably having a pore volume of from 0.05 to 1.0 $cm^3/g$ and a surface area of from 0.01 to 1.0 $m^2/g$. Preferably, the large porous carrier particles have a spherical or ring-like (toroidal) shape.

For the purpose of making channels in the catalyst to be used according to the present invention, as described in EP-A 0 510 566, one can use both natural and synthetic organic fibers (textile fibers), made from carbon-based compounds. Alternatively, carbon fibers, which result from carbonization and graphitization of natural and synthetic organic fibers, may be used to make channels in the present catalyst. During calcining in a temperature range of between 100° and 380° C., the fibers are destroyed, particularly in the presence of oxygen, and, in the end, they are broken down into gaseous products, leaving behind cavities that correspond essentially to the dimensions of the fibers. Natural fibers include, for example, cotton, wool, and cellulose derivatives. Organic fibers include those made of polyamides (nylon), polyester, polyolefins or acrylonitrile.

The fibers to be used should have a diameter of from 1 to 100 $\mu m$, particularly from 5 to 70 $\mu m$, above all from 15 to 50 $\mu m$. The fibers to be used should have a length which may be a multiple of the diameter of the final catalyst particle, such as, for example, from 1 to 30 mm, preferably from 1 to 10 mm, particularly preferably from 2 to 8 mm, above all from 3 to 6 mm. They are added in quantities of from 0.5 to 5% by weight, especially from 1 to 4% by weight, and above all from 1.5 to 3.5% by weight, relative to the amount of catalytically active material that is present in the catalyst.

A Process for Producing Methacrylic Acid and Methacrolein by Oxidation of Isobutane Isobutane is oxidized using the previously described catalysts with molecular oxygen at a temperature in the range of from 250° to 450° C. especially from 300° to 450° C., more preferably from 320° to 400° C. The initial oxygen-containing gas is added in an amount which provides from 0.2 to 10 mole, and especially from 0.5 to 5 mole, of oxygen per mole of isobutane. Oxygen may be introduced, for example, in the form of air or in the form of oxygen-enriched air. Additional gases which may be introduced into the reactor may include nitrogen and inert gases. Additional gases may also include CO, $CO_2$ and water vapor, which may be present in total in a volume of from 0 to 10 mol per mol of isobutane. The reaction gases may advantageously be recycled.

The reaction can be performed over a wide pressure range, from negative pressure up to overpressure. Preferably, the reaction pressure is from about 0.1 to 10 atmospheres absolute (atm abs), more preferably from 0.5 to 5 atm abs, and in particular from 0.8 to 3 atm abs.

The present oxidation is advantageously performed in a packed-bed reactor, in the form of one or more tube reactors. The oxidation can also be performed in reactors with a moving catalyst bed, and in reactors with a fluidized bed.

Methacrylic acid and methacrolein are obtained and purified from the reaction gas exiting from the reactor according to known methods, such as condensation, extraction, and distillation. Unconverted isobutane is returned to the oxidation process, advantageously with other gaseous and inert compounds, such as CO, $CO_2$, nitrogen, and water vapor (by circulating gas control).

To make methacrylic acid, an essential valuable product, it is then furthermore advantageous to separate the formed methacrolein, and to pipe it together with isobutane over the catalyst. The heteropoly acid catalysts used according to the present invention are known and effective catalysts for the oxidation of methacrolein into methacrylic acid. Accordingly, methacrylic acid can be produced from isobutane on an industrial scale in a reactor system.

The retention time, and thus also, the reciprocal value of the catalyst load is expressed quantitatively by the quotient W/F, with the dimension given in terms of hours (hr), where W (weight) is the weight of the catalytically active mass and F (feed) is the weight of the starting material to be converted per hour, such as that of isobutane, possibly with methacrolein in equal weight units.

TABLE 1

|  | W/F (hr) | Isobutane | Molar Ratio $O_2:N_2:H_2O$ |
| --- | --- | --- | --- |
| Condition 1 | 4.1 | 1.15 | 4.5:6.55:3 |
| Condition 2 | 2.1 | 2.3 | 4.5:5.4:3 |
| Condition 3 | 1.0 | 4.6 | 4.5:3.1:3 |

TABLE 2

Results from the oxidation of isobutane on $Cu_{2.0}H_{3.6}PMo_{11}VO_{40}$
(Conditions according to TABLE 1)

| Example Number | Condition | Temperature (°C) | Isobutane Conversion (%) | MAA Sel. (%) | MAA RZA (g/L·h) | Methacrolein Sel. (%) | Methacrolein RZA (g/L·h) | Total Selectivity (%) |
| --- | --- | --- | --- | --- | --- | --- | --- | --- |
| 1 | 1 | 327.5 | 5.3 | 56.6 | 4.3 | 23.6 | 1.43 | 80.2 |
| 2 | 2 | 331.5 | 9.5 | 59.3 | 18.8 | 17.0 | 3.7 | 86.3 |
| 3 | 2 | 347.9 | 13.0 | 55.6 | 20.65 | 11.5 | 3.42 | 67.1 |
| 4 | 3 | 328.0 | 4.4 | 50.5 | 12.7 | 31.0 | 6.23 | 81.5 |

Other features of the invention will become apparent in the course of the following descriptions of exemplary embodiments which are given for illustration of the invention and are not intended to be limiting thereof. In the examples given below, the present process is described with improved, and above all, more selective P—Mo—V-containing heteropoly acid catalysts. The results are given for the determined selectivities (Sel.) for methacrylic acid (MA) and methacrolein, and for the space-time yields of these oxidation products.

EXAMPLE 1

To 1,500 g of $SiO_2$ carrier material, 6 liters of an aqueous 45 wt. % solution of heteropoly acids having a $Cu_{0.2}H_{3.6}PMo_{11}VO_{40}$ stoichiometry were added and stirred for 10 min at the boiling temperature of the heteropoly acid solution (about 100° C.). The carrier covered with heteropoly acid was then isolated by suction filtration, and dried. An $SiO_2$ carrier, covered with 43% $Cu_{0.2}H_{3.6}PMo_{11}VO_{40}$ as the catalytically active material, was recovered. The covered catalyst was then calcined in air for 4 hours at 300° C. The catalyst was then inserted into a gas-phase reactor for the gas phase oxidation of isobutane. The components of the gaseous reaction mixture consisting of isobutane, oxygen, nitrogen, and water vapor, each employed at certain molar ratios as described in Table 1 below, were passed over this catalyst. The retention times employed (weight/feed=W/F (hr)) are also recited in Table 1 below. The results are presented in Table 2 below, in which "RZA" refers to the space-time yield.

EXAMPLE 2

Another catalyst used during the oxidation of isobutane was a contact consisting of a $SiO_2$ carrier and 45% $H_8PMo_{10}VO_{39}$ as the catalytically active component. The catalyst of Example 2 was prepared as described in Example 1, but $H_8PMo_{10}VO_{39}$ was substituted for the $Cu_{0.2}H_{3.6}PMo_{11}VO_{40}$ heteropoly acid. As in Example 1, the $SiO_2$ carrier particles had a spherical form with an average particle size of 5 mm, a total pore volume of 0.535 cm$^3$/g and a surface area of 0,111 m$^2$/g.

The results illustrated in Table 4 were obtained with the molar ratios of the gaseous reactants given in Table 3.

TABLE 3

|  | W/F (hr) | Isobutane | Molar Ratio $O_2:N_2:H_2O$ |
| --- | --- | --- | --- |
| Condition 4 | 3 | 3 | 3:2:2 |
| Condition 5 | 3 | 3 | 3:0:2 |

Obviously, numerous modifications and variations of the present invention are possible in light of the above teachings. It is therefore to be understood that within the scope of the appended claims, the invention may be practiced otherwise than as specifically described herein.

TABLE 4

Results from the oxidation of isobutane on $H_8PMo_{10}VO_{39}$
(Conditions according to TABLE 3)

| Example Number | Condition | Temperature (°C) | Isobutane Conversion (%) | MAA Sel. (%) | MAA RZA (g/L·h) | Methacrolein Sel. (%) | Methacrolein RZA (g/L·h) | Total Selectivity (%) |
| --- | --- | --- | --- | --- | --- | --- | --- | --- |
| 5 | 4 | 330.7 | 2.3 | 13.3 | 0.9 | 77.2 | 3.9 | 90.5 |
| 6 | 4 | 351.2 | 3.5 | 18.4 | 1.8 | 67.4 | 5.2 | 85.8 |
| 7 | 4 | 361.4 | 4.0 | 24.4 | 2.7 | 58.0 | 5.1 | 82.4 |
| 8 | 4 | 370.1 | 5.1 | 30.1 | 4.2 | 50.2 | 5.1 | 80.3 |
| 9 | 5 | 341.1 | 4.1 | 19.3 | 2.4 | 63.2 | 6.1 | 82.5 |
| 10 | 5 | 350.8 | 4.6 | 22.1 | 2.8 | 59.3 | 6.0 | 81.4 |
| 11 | 5 | 370.6 | 7.6 | 29.6 | 6.2 | 41.4 | 6.9 | 71.0 |

What is claimed as new and desired to be secured by Letters Patent of the United States is:

1. A process for making methacrylic acid and methacrolein, comprising oxidizing isobutane with molecular oxygen in the gaseous phase at a temperature of from 250° to 450° C. on a solid heteropoly acid catalyst having a formula selected from the group consisting of the formula (I)

$$CU_aH_bP_cMo_dV_eO_f \quad (I)$$

where $a=0.1$ to 1, $b=0$ to 7.8, $c=0.8$ to 1.2, $d=9$ to 12, $e=0.5$ to 3, and f depends on the molar numbers a to e, the formula (II)

$$H_8PMo_{10}VO_{39} \quad (II),$$

its anhydride (III)

$$PMo_{10}VO_{35} \quad (III),$$

a mixture of the catalyst of the formula (I) with the catalyst of the formula (II) and mixture of the catalyst of the formula (I) with the catalyst of the formula (III).

2. The process of claim 1, said heteropoly acid catalyst having the formula (I)

$$CU_aH_bP_cMo_dV_eO_f \quad (I)$$

where $a=0.1$ to 1, $b=0$ to 7.8, $c=1$, $d=10$ or 11, $e=1$ or 2, and f depends on the molar number a to e.

3. The process of claim 1, said catalyst having the formula (II)

$$H_8PMo_{10}VO_{39} \quad (II)$$

or its anhydride (III)

$$PMo_{10}VO_{35} \quad (III).$$

4. The process of claim 1, wherein said oxidizing is performed in the presence of a gas selected from the group consisting of nitrogen, carbon dioxide, water vapor, and mixtures thereof.

5. The process of claim 1, wherein said isobutane further contains methacrolein.

* * * * *